United States Patent [19]

Katsurada et al.

[11] Patent Number: 5,188,948
[45] Date of Patent: Feb. 23, 1993

[54] PROCESS FOR PRODUCING L-VALINE BY FERMENTATION

[75] Inventors: Naoki Katsurada, Kanagawa; Haruo Uchibori; Takayasu Tsuchida, both of Kawasaki, all of Japan

[73] Assignee: Ajinomoto Co., Inc., Tokyo, Japan

[21] Appl. No.: 478,032

[22] Filed: Feb. 9, 1990

Related U.S. Application Data

[63] Continuation of Ser. No. 180,551, Apr. 12, 1988, abandoned.

[30] Foreign Application Priority Data

Apr. 16, 1987 [JP] Japan ............................. 62-093959

[51] Int. Cl.$^5$ .................. C12P 13/08; C12N 15/00; C12N 1/20
[52] U.S. Cl. ............................ 435/115; 435/172.1; 435/252.1; 435/840; 435/843
[58] Field of Search ................. 435/115, 172.1, 840, 435/252.1, 843

[56] References Cited

U.S. PATENT DOCUMENTS

| 3,893,888 | 7/1975 | Tsuchida et al. | 435/115 |
| 4,666,840 | 5/1987 | Olivieri et al. | 435/227 |

FOREIGN PATENT DOCUMENTS

| 2604447 | 4/1988 | France | 435/115 |
| 7005691 | 1/1982 | Japan | 435/115 |
| 036197 | 2/1987 | Japan | 435/115 |

OTHER PUBLICATIONS

The Merck Index, 1983, 10th ed., p. 174.
Bu'lock, J. D., Compr. Org. Chem., vol. 5, pp. 927–987, 1979, Pergamon Press.

*Primary Examiner*—Irene Marx
*Attorney, Agent, or Firm*—Oblon, Spivak, McClelland, Maier & Neustadt

[57] ABSTRACT

A process for producing L-valine by fermentation which comprises culturing in a liquid culture medium an L-valine producing microorganism which belongs to the genus Brevibacterium or Corynebacterium and which is resistant to a polyketide, and then recovering L-valine accumulated in said culture medium.

4 Claims, No Drawings

PROCESS FOR PRODUCING L-VALINE BY FERMENTATION

This application is a continuation of application Ser. No. 07/180,551, filed on Apr. 12, 1988, now abandoned.

BACKGROUND OF THE INVENTION

1. Field of the Invention

L-valine is an important ingredient for amino acid infusions and for general amino acid formulations. The present invention relates to an improved process for producing L-valine by fermentation.

2. Discussion of the Related Art

It is known that certain microorganisms of the genera *Brevibacterium* and *Corynebacterium* have the ability to produce L-valine when they are provided with the property of requiring L-isoleucine, L-leucine, L-homoserine, etc., or with resistance to norvaline, 2-thiazolealanine, α-aminobutyric acid, etc. However, there remains a need to improve the yield of fermentation and to lower the cost for the production of L-valine.

SUMMARY OF THE INVENTION

Accordingly, an object of the present invention is to discover new means for low cost production of L-valine.

It is yet another object of the present invention to improve the yield of L-valine obtained by fermentation.

To achieve the above objects, the present inventors have searched for additional strains which are capable of producing L-valine in a higher yield.

In order to discover such strains, the inventors carried out intensive studies for the improvement of known L-valine producing microorganisms of the genera *Brevibacterium* and *Corynebacterium*. As a result, among strains exhibiting resistance to polyketides, there were found mutants capable of producing L-valine in a higher yield than that of the prior L-valine producing strains.

Accordingly, there is provided by the present invention a process for producing L-valine which comprises culturing in a liquid medium an L-valine producing microorganism which belongs to the genus *Brevibacterium* or *Corynebacterium* and which is resistant to a polyketide, and then recovering L-valine accumulated in said culture medium.

DETAILED DESCRIPTION OF THE PREFERRED EMBODIMENTS

Many polyketides are already known, including, e.g., triacetic acid lactone, mycophenolic acid, terrin, cerulenin, fallacinal, frenolicin, solorinic acid, and the like. Resistance to one or a combination of polyketides is suitable for the present invention.

Microorganisms which can be used in the present invention are mutants of the genus *Brevibacterium* or *Corynebacterium* having resistance to one or more polyketides and having the ability to produce L-valine. In order to obtain mutants according to the invention, wild strains, such as those set forth hereinbelow, may be provided with the ability of producing L-valine and then rendered resistant to polyketides, or such wild strains may be first rendered resistant to polyketides and then provided with the ability of producing L-valine.

Wild strains which may be used as a parent strain for the mutants according to the invention include microorganisms of the genera *Brevibacterium* and *Corynebacterium*, in particular those known as L-glutamic acid producing strains. Examples of such microorganisms include the following:

*Brevibacterium divaricatum* ATCC 14,020
*Brevibacterium flavum* ATCC 14,067
*Brevibacterium lactofermentum* ATCC 13,869
*Brevibacterium saccharolyticum* ATCC 14,066
*Corynebacterium acetoacidophilum* ATCC 13,870
*Corynebacterium glutamicum* ATCC 13,032

In order to induce the mutation of such a parent strain, there can be utilized any of the known mutation techniques, including the one employing N-methyl-N'-nitro-N-nitrosoguanidine. Mutants according to the invention can be obtained by culturing strains subjected to mutation in a medium containing polyketides and then recovering those capable of growth in said medium.

The mutation induction method employed to obtain the mutants according to the invention is specifically described hereinbelow.

Method for Inducing Mutation

*Brevibacterium lactofermentum* AJ 3434 (FERM-P 1845, resistant to 2-thiazolealanine and requiring isoleucine and methionine) or *Corynebacterium glutamicum* AJ 3776 (FERM-P 2601) [see Japanese Patent Application (Laid Open) No. 155,684/75] was cultured on a bouillon agar slant at 30° C. for 24 hours, and the cells were suspended in M/30 phosphate buffer to form a suspension containing $10^8$ to $10^9$/ml of cells. To this suspension was added 500 g/ml of N-methyl-N'-nitro-N-nitrosoguanidine, and the resulting suspension was maintained at 30° C. for 20 minutes. The cells were collected by centrifugation, washed well with M/30 phosphate buffer, inoculated on a medium having the composition set forth below and then cultured at 31.5° C. for a period of from 4 to 10 days.

| Composition of the Medium (pH 7.0) | |
|---|---|
| Ingredients | Amount |
| Glucose | 2.0 g/dl |
| Urea | 0.2 g/dl |
| $(NH_4)_2SO_4$ | 0.5 g/dl |
| $K_2HPO_4$ | 0.1 g/dl |
| $KH_2PO_4$ | 0.1 g/dl |
| $MgSO_4.7H_2O$ | 0.001 g/dl |
| $MnSO_4.7H_2O$ | 0.001 g/dl |
| Biotin | 50 μg/l |
| Thiamin hydrochloride | 100 μg/l |
| L-isoleucine | 0.3 g/dl |
| DL-methionine | 0.1 g/dl |
| MPA (Mycophenolic acid) | 0.1 g/dl |
| Agar | 2.0 g/dl |

There were obtained *Brevibacterium lactofermentum* AJ 12,341 (FERM-P 9324, FERM-BP-1763) and *Corynebacterium glutamicum* AJ 12,342 (FERM-P 9325, FERM BP-1764) be selecting colonies capable of growth on the medium and having a high productivity of L-valine.

The resistance to MPA of the thus obtained mutants was compared with that of the parent strains.

Each of the strains were cultured on a slant of a natural medium (containing 1 g/dl of peptone, 1 g/dl of a yeast extract and 0.5 g/dl of NaCl and having a pH of 7.0) for 24 hours, and then the cells were suspended in sterilized water. The suspended cells were inoculated in a medium containing 1.0 g/dl of glucose, 0.15 g/dl of urea, 0.3 g/dl of ammonium sulfate, 0.1 g/dl of K₂HPO₄, 0.1 g/dl of KH₂PO₄, 0.05 g/dl of MgSO₄•7H₂O, 0.001 g/dl of FeSO₄•7H₂O, 0.001 g/dl of MnSO₄•7H₂O, 50 µg/dl of biotin, 100 g/l of thiamin hydrochloride, 0.1 g/dl of L-isoleucine, 0.1 g/dl of DL-methionine and MPA in an amount shown in Table 1 and, after 24 hours incubation, the degree of growth of the cells was determined by means of turbidity.

The mutants identified as FERM P-9324 and FERM P-9325 were originally deposited on Apr. 9, 1987 at the Fermentation Research Institute, Agency of Industrial Science and Technology, Ministry of International Trade and Industry (FRI), 1-3, Higashi 1-chome, Tsukuba-shi, Ibaragi-ken 305, Japan. The mutant deposits were then converted into deposits under the Budapest Treaty on Feb. 26, 1988, and were accorded the corresponding deposit numbers FERM BP-1763 and FERM-BP-1764.

TABLE 1

| Strain | MPA (%) | | | | |
|---|---|---|---|---|---|
| | 0 | 0.005 | 0.01 | 0.05 | 0.1 |
| AJ 3434 | 100 | 90 | 35 | 0 | 0 |
| AJ 12341 (FERM BP-1763) | 100 | 100 | 82 | 30 | 5 |
| AJ 3776 | 100 | 85 | 20 | 0 | 0 |
| AJ 12342 (FERM BP-1764) | 100 | 100 | 65 | 5 | 0 |

In many cases, a further improved yield can be attained by additionally providing the above mutants with such properties as resistance to norvaline, resistance to 2-thiazolealanine, resistance to α-aminobutyric acid, etc., which are already known to be effective for the improvement of productivity of L-valine.

The microorganisms can be cultured in an ordinary medium containing carbon sources, nitrogen sources, inorganic ions and, where necessary, trace amounts of other organic nutrients.

As carbon sources, there can be used glucose, sucrose, organic acids (such as acetic acid), and the like.

As nitrogen sources, there can preferably be used ammonia gas, ammonium salts, urea, etc.

Cultivation of the cells is preferably carried out under aerobic conditions. Better results can be attained if, during the cultivation, the pH of the medium is maintained at from 4 to 8 and the temperature at from 25° to 37° C.

Thus, a large amount of L-valine can be accumulated in the medium after 1 to 7 days of cultivation.

The thus formed L-valine can be recovered from the medium by a conventional method utilizing, e.g., an ion exchange resin.

The invention will now be more specifically described in terms of examples, which are included herein for purposes of illustration only and are not intended to be limiting of the present invention, except as stated hereinbelow.

EXAMPLES

Example 1

The pH of a seed medium containing 3 g/dl of glucose, 0.1 g/dl of KH₂PO₄, 0.04 g/dl of MgSO₄•7H₂O, 0.001 g/dl of MnSO₄•7H₂O, 0.3 g/dl of urea, 0.13 g/dl (as total nitrogen) of hydrolysate of bean protein, 10 µg/dl of biotin, 300 µg/l of thiamin HCl and 0.01 g/dl of DL-methionine was adjusted to 6.5. Into shouldered 500 ml flasks were placed 500 ml each of the seed medium, and then the medium was sterilized. Each of the flasks was inoculated with a strain shown in Table 1, and its culturing was carried out with shaking for 20 hours, during which the temperature of the medium was maintained at 31.5° C.

Into 1 liter fermenters was placed 285 ml each of a medium (adjusted to a pH of 6.5) containing 15 g/dl of glucose, 0.1 g/dl of KH₂PO₄, 0.04 g/dl of MgSO₄•7H₂O, 0.001 g/dl of FeSO₄•7H₂O, 0.001 g/dl of MnSO₄•7H₂O, 2.0 g/dl of ammonium sulfate, 0.08 g/dl (as total nitrogen) of hydrolysate of soybeans, 5 µg/dl of biotin, 30 µg/l of thiamin HCl and 60 mg/dl of DL-methionine, and the contents were sterilized. To the resulting medium was inoculated with 15 ml each of the above seed medium. Its culturing was carried out with shaking and aeration at a temperature of 31.5° C. until the concentration of glucose decreased to 0.5 g/dl or less, during which the pH of the medium was maintained at 6.5 to 7.0 by the addition of ammonia gas.

L-valine was obtained in the yields (based on the weight of glucose) shown in Table 2.

TABLE 2

| Tested Strain | Yield of L-Valine (%) |
|---|---|
| AJ 3434 | 20 |
| AJ 12341 | 28 |
| AJ 3776 | 19 |
| AJ 12342 | 26 |

*Bervibacterium lactodermentum* AJ 12341 was cultured in the same manner as above. There was obtained 1 liter of cultured broth which was then subjected to centrifugation to remove cells. The supernatant obtained was passed through a column of a strongly acidic ion exchange resin (Dia Ion SK-1B, NH₄⁺ type). The resin was washed with water and eluted with 2N ammonia water, and the eluent was condensed to obtain 19 g of L-valine.

Example 2

Into 1 liter jar fermenters was charged 300 ml each of a medium having the composition set forth below, and then the contents of the fermenters were sterilized.

| Composition of Fermentation Media: | | |
|---|---|---|
| | Seed Medium | Medium for Main Fermentation |
| Glucose (g/dl) | 1.5 | — |
| Ammonium acetate (g/dl) | 0.3 | 0.3 |
| KH₂PO₄ (g/dl) | 0.15 | 0.2 |
| MgSO₄.7H₂O (g/dl) | 0.04 | 0.1 |
| Fe⁺⁺ (ppm) | 2 | 2 |
| Mn⁺⁺ (ppm) | 2 | 2 |
| Hydrolysate of soybeans (g/l) (Total nitrogen, 6.4 g/dl) | 3 | 2 |
| Biotin (γ/l) | 100 | 100 |
| Vitamin B₁ Hydrochloride (γ/l) | 100 | 100 |
| Ammonium sulfate (g/dl) | — | 1 |
| Urea (g/dl) | 0.2 | — |
| DL-methionine (mg/dl) | 60 | 60 |
| pH | 8.0 | 7.2 |

Strains set forth in Table 3 were cultivated with shaking for 24 hours in the above-described seed medium, and the seed cultures obtained were separately inoculated in each medium contained in the fermenters at a percentage of 5% and cultured at 31° C. with a stirring rate of 1,500 rpm and an aeration of 1/1 VVM.

During the cultivation, a 1:0.20 (by weight) amount of acetic acid and ammonium acetate (concentration of acetic acid, 70 g/dl) was added to the medium so as to maintain its pH at 7.5 and, at the same time, to supply the carbon source. After 90 hours of cultivation, L-valine was accumulated in yields shown in Table 3 (based on the weight of acetic acid consumed). After the completion of the fermentation by strain AJ 12341, the cells were removed by the conventional method to obtain 15 g of crude crystals of L-valine, per liter of culture medium.

TABLE 3

| Tested Strain | Yield (%) of L-Valine Based on the Weight of Acetic Acid |
| --- | --- |
| AJ 3434 | 8 |
| AJ 12341 | 12 |
| AF 3776 | 7 |
| AJ 12342 | 10 |

The invention now being fully described, it will be understood to one of ordinary skill in the art that the invention may be practiced otherwise than a described herein.

What is claimed as new and is desired to be secured by Letters Patent of the United States is:

1. A process for producing L-valine by fermentation, which comprises culturing in an aqueous nutrient medium containing assimilable sources of carbon, nitrogen and inorganic substances an L-valine producing microorganism which is selected from the group consisting of *Brevibacterium lactofermentum* AJ 12341 (FERM BP-1763) and *Corynebacterium glutamicum* AJ 12342 (FERM BP-1764), and then recovering L-valine accumulated in said aqueous nutrient medium.

2. The process according to claim 1, wherein culturing of said microorganism in said culture medium is carried out under aerobic conditions at a pH of from 4 to 8 and a temperature of from 25° to 37° C.

3. The process according to claim 2, wherein said culturing is carried out for from 1 to 7 days.

4. The process according to claim 1, wherein L-valine is recovered by applying said culture medium to an ion exchange resin.

* * * * *